United States Patent
Joseph

(10) Patent No.: US 10,300,162 B2
(45) Date of Patent: May 28, 2019

(54) DISINFECTANT WIPE DISPENSER

(71) Applicant: PERACIDE (UK) LIMITED, Sheffield (GB)

(72) Inventor: Michael Joseph, Sheffield (GB)

(73) Assignee: PERACIDE (UK) LIMITED, Sheffield (GB)

(*) Notice: Subject to any disclaimer, the term of this patent is extended or adjusted under 35 U.S.C. 154(b) by 72 days.

(21) Appl. No.: 15/517,609

(22) PCT Filed: Oct. 6, 2015

(86) PCT No.: PCT/GB2015/052911
§ 371 (c)(1),
(2) Date: Apr. 7, 2017

(87) PCT Pub. No.: WO2016/055773
PCT Pub. Date: Apr. 14, 2016

(65) Prior Publication Data
US 2017/0304478 A1    Oct. 26, 2017

(30) Foreign Application Priority Data

Oct. 7, 2014    (GB) .................................. 1417731.5

(51) Int. Cl.
*A61L 2/26*     (2006.01)
*A47K 10/42*    (2006.01)
(Continued)

(52) U.S. Cl.
CPC ............ *A61L 2/26* (2013.01); *A47K 10/3818* (2013.01); *A47K 10/421* (2013.01); *A61L 2/18* (2013.01); *A47K 2010/3273* (2013.01)

(58) Field of Classification Search
CPC ......... A61L 2/26; A61L 2/18; A47K 10/3818; A47K 10/421; A47K 2010/3273
(Continued)

(56) References Cited

U.S. PATENT DOCUMENTS 4,262,816 A * 4/1981 Margulies .......... A47K 10/3818
206/409
5,273,184 A * 12/1993 Rizzuto .............. A47K 10/3818
221/286
(Continued)

FOREIGN PATENT DOCUMENTS

EP    1364610    11/2003
EP    1755387    11/2012
(Continued)

OTHER PUBLICATIONS

WO2015107342 Written Opinion, dated Jul. 23, 2015, Peracide (UK) LTD.
(Continued)

*Primary Examiner* — Michael Collins
(74) *Attorney, Agent, or Firm* — Brian S. Boyer; Syndicated Law, PC

(57) ABSTRACT

A disinfectant wipe dispenser is provided comprising a container having first and second compartments, the first compartment being dimensioned to store a supply of wipes in use; and, separated by a baffle including one or more channels communicating between the compartments. The first compartment has an outlet through which wipes may be successively drawn; and, the second compartment is dimensioned to receive one or more portions of a disinfectant composition comprising a peroxy activator, a peroxy compound and optional further excipients, selected so that addition of the dosage form to a predetermined quantity of water produces a disinfectant solution containing peracetic acid at a concentration of at least about 1000 ppm. The channels communicate between the compartments and allow flow of water and aqueous disinfectant between the compartments, and have a maximum dimension configured to
(Continued)

prevent movement of particles of disinfectant sediment from the second compartment to the first compartment.

19 Claims, 8 Drawing Sheets

(51) Int. Cl.
    *A61L 2/18*     (2006.01)
    *A47K 10/38*     (2006.01)
    *A47K 10/32*     (2006.01)

(58) Field of Classification Search
    USPC .......................................................... 221/34
    See application file for complete search history.

(56) References Cited

U.S. PATENT DOCUMENTS

| | | | |
|---|---|---|---|
| 5,407,685 A | 4/1995 | Malchesky et al. | |
| 6,158,614 A * | 12/2000 | Haines | A47K 10/3818 221/33 |
| 6,210,639 B1 | 4/2001 | Gayle et al. | |
| 7,291,276 B1 | 11/2007 | Neal | |
| 7,534,756 B2 * | 5/2009 | Tichy | A01N 59/16 510/161 |
| 7,806,291 B2 * | 10/2010 | Anderson | A47K 10/3818 221/33 |
| 2003/0122031 A1 * | 7/2003 | Tramontina | A47K 10/3818 242/593 |
| 2003/0129254 A1 | 7/2003 | Yasuhara et al. | |
| 2006/0124476 A1 | 6/2006 | Sivakumar et al. | |
| 2007/0241022 A1 | 4/2007 | Denome et al. | |
| 2008/0000931 A1 | 1/2008 | Tichy et al. | |
| 2008/0160057 A1 | 7/2008 | Fellows | |
| 2010/0075883 A1 | 3/2010 | Geret et al. | |
| 2010/0124784 A1 | 5/2010 | Read | |
| 2011/0177148 A1 | 7/2011 | Dicosimo et al. | |
| 2013/0259957 A1 | 10/2013 | Dagher et al. | |
| 2016/0330971 A1 | 11/2016 | Joseph | |

FOREIGN PATENT DOCUMENTS

| | | |
|---|---|---|
| EP | 2692844 | 2/2014 |
| FR | 2883478 | 9/2006 |
| GB | 2506412 | 9/2012 |
| TW | 200815056 | 4/2008 |
| WO | WO 2005/112631 | 12/2005 |
| WO | WO 2008/060778 | 5/2008 |
| WO | WO 2008/079170 | 7/2008 |
| WO | WO 2011/161396 | 12/2011 |
| WO | WO2015107342 | 7/2015 |
| WO | WO2016055773 | 4/2016 |

OTHER PUBLICATIONS

WO2016055773 Written Opinion, dated Apr. 14, 2016, Peracide (UK) LTD.

* cited by examiner

DISINFECTANT WIPE DISPENSER

CROSS-REFERENCE TO RELATED APPLICATIONS

This application is a National Stage of International Application No. PCT/GB2015/052911, filed Oct. 6, 2015, which claims the benefit of GB 1417731.5, filed Oct. 7, 2014, each of which is incorporated herein by reference in its entirety.

BACKGROUND

Field of the Invention

This invention relates to a disinfectant and sanitising wipe dispenser particularly but not exclusively of the kind for dispensing wipes used for disinfecting and sanitising surfaces or clinical equipment in hospitals or other medical treatment facilities. The dispenser may also be used in domestic or commercial environments.

Description of Related Art

The invention particularly relates to dispensers for use with wipes which are impregnated with peracetic acid containing disinfectant solutions. These solutions are unstable and must be formed before use by dissolution in water of a solid precursor composition. An important factor is that peracetic acid solutions must reach a minimum working concentration of peracetic acid before use and must remain at such a concentration during use in order to ensure effective disinfectant and sanitising of the surfaces or equipment to which it is applied.

Our UK patent application number 1400596.1 discloses a solid disinfectant dosage form comprising a peroxy activator, and a peroxy compound selected so that addition of the dosage form to a predetermined quantity of water produces a disinfectant solution containing peracetic acid in a concentration of at least about 1000 ppm. Preferred embodiments further comprise a colour indicator system arranged to provide a first colour signal when the concentration of peracetic acid is lower than about 1000 ppm, a second colour signal when the concentration is higher than about 1000 ppm and a third colour signal when the concentration falls below about 1000 ppm.

Disinfectant wipe dispensers commonly used in hospital, household and commercial environments comprise a container having a cap through which the wipes may be drawn successively as required. The wipes are moistened with a disinfectant composition. Such compositions, which may be stored for prolonged periods before use, may have insufficient activity to ensure a high degree of sterilisation as required in a hospital environment. In addition, commonly used disinfectant wipe dispensers do not prevent build up of disinfectant sediment onto the wipes. Build up of disinfectant sediment onto wipes may result in wipes exhibiting unsafe levels of disinfectant activity, and may also cause scratches on polished surfaces.

SUMMARY

According to the present invention a disinfectant wipe dispenser comprises:

a container having first and second compartments, the first compartment being dimensioned to store a supply of wipes in use;

the first and second compartments being separated by a baffle, the baffle including one or more channels communicating between the compartments;

the first compartment having an outlet through which wipes may be successively drawn;

the second compartment being dimensioned to receive one or more portions of a disinfectant composition, the disinfectant composition comprising a peroxy activator, a peroxy compound and optional further excipients, selected so that addition of the dosage form to a predetermined quantity of water produces a disinfectant solution containing peracetic acid at a concentration of at least about 1000 ppm;

wherein the channels communicate between the compartments and allow flow of water and aqueous disinfectant between the compartments;

wherein the channels have a maximum dimension configured to prevent movement of particles of disinfectant sediment from the second compartment to the first compartment.

BRIEF DESCRIPTION OF THE DRAWINGS

Preferred embodiments will now be described by way of example only, with reference to the accompanying drawings, in which.

DETAILED DESCRIPTION

Figure 1:
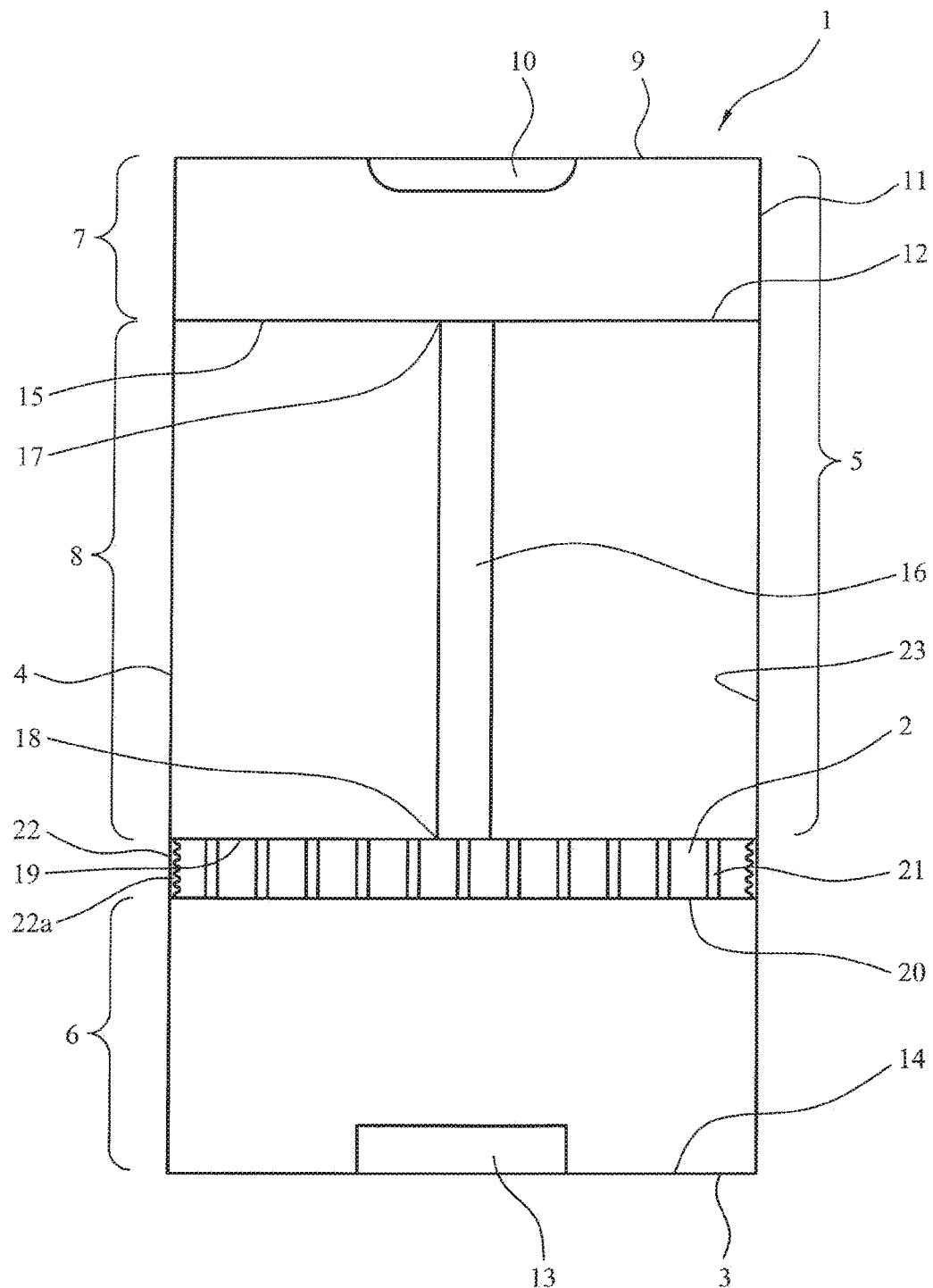
FIG. 1 shows a side view of the container where the baffle is connected to the first sub-compartment through the use of an arm.

The container may be dimensioned to receive the predetermined quantity of water to produce an effective concentration of peracetic acid.

The container may be dimensioned so that the wipes are immersed when the predetermined amount of water is added. The container may have a marking to indicate the water level when the correct predetermined amount has been added.

The dosage form may comprise a colour indicator system arranged to provide a colour signal when the concentration of peracetic acid in the container is higher than about 1000 ppm, the container being at least partially transparent to permit observation of the colour signal.

The threshold concentration of peracetic acid may be lower than about 4000 ppm for the first, second and optional third colour signals.

The container may have a cylindrical shape, the baffle being circular in plan view and dimensioned to form a friction fit within the container. In such an embodiment the second compartment is located below the baffle. In use the baffle may be removed and one or more dosage forms inserted into the second, lower compartment of the container, followed by replacement of the baffle and insertion of a supply of wipes to the first compartment above the baffle.

The outlet may be closeable by means of a detachable cap.

The container may comprise inwardly extending ridges. The inwardly extending ridges may be located at the base of the container.

In an alternative embodiment the container may have a fixed baffle with separate openings to each compartment being closable by one or more caps. For example a cylindrical container may have an opening at either end. Alternatively a single opening may permit access to both compartments, the compartments being separated by an upwardly extending baffle.

The baffle may be configured to permit flow of aqueous disinfectant, while retaining undissolved particles of the composition within the second compartment. Eliminating build up of disinfectant sediment onto the wipes may result in the wipes having safe disinfectant activity and avoids any risk of scratching polished surfaces while being wiped.

The container may further include a receptacle. The receptacle may comprise: a side wall, outlet, base and one or more channels through which aqueous disinfectant may flow, the outlet of the receptacle being configured to engage with the baffle.

The receptacle may be provided in the second compartment to receive one or more portions of the disinfected composition. The receptacle is preferably dimensioned and configured to receive each portion, permitting liquid flow around the portion to formulate rapid dissolution.

The seal between the baffle and the outlet of the receptacle may be provided through a friction fit.

Alternatively, the seal may be provided through threaded engagement between the baffle and the outlet of the receptacle.

In one embodiment the one or more channels may extend through the base of the receptacle. The channels allow liquid to enter and exit the receptacle and thereby facilitate the disintegration of the one more portions of soluble disinfectant. The channels further restrict the outflow of solid particles.

Additionally, the one or more channels may extend through the side walls of the receptacle. The channels allow liquid to enter and exit the receptacle and thereby facilitate the disintegration of the one more portions of soluble disinfectant compositions. The channels further restrict the outflow of solid particles.

Alternatively, the one or more channels may extend through the base and the side walls of the receptacle. The channels allow liquid to enter and exit the receptacle and thereby facilitate the disintegration of the one more portions of soluble disinfectant. The channels further restrict the outflow of solid particles.

The channels of the receptacle may have maximum diameters in the range from 1 mm to 5 mm.

Alternatively, the channels of the receptacle may have maximum diameters in the range from 0.1 mm to 1 mm.

The receptacle may include one or more microporous filter pads. The pads may be secured to the receptacle so that they which cover at least a portion of the receptacle channels. The microporous filter pads may permit flow of aqueous disinfectant, while retaining undissolved particles of the composition within the second compartment. One microporous filter pads may be attached to the base of the receptacle to cover all channels located in the base of the receptacle.

Additionally, one or more elongate microporous filter pads may be located adjacent the side wall of the receptacle to cover all channels located in the side wall of the receptacle.

When the receptacle channels are located in both the side wall and base of the receptacle, one microporous filter pad may be attached to the base of the receptacle and one elongated micro porous filter pad may be attached to the side wall of the receptacle, thereby covering all the receptacle channels.

Alternatively, one or more microporous filter pads may overlap along the side wall and base of the receptacle, thereby covering all the receptacle channels.

Alternatively, one or more microporous filter pads may overlap along the side wall and base to cover only a portion of the receptacle channels.

The one or more microporous filter pads of the receptacle may have a plurality of pores extending therethrough, the pores may have maximum diameters in the range from 0.1 µm to 50 µm, 0.1 µm to 20 µm, or 0.1 µm to 10 µm.

In a preferred embodiment the receptacle contains a plurality of chambers, each being dimensioned to receive one or more portions of soluble disinfectant composition.

The receptacle may contain three chambers, wherein each chamber may be dimensioned to receive one respective portion of soluble disinfectant composition.

The plurality of chambers may be of any conveniently manufactured shape or size. Additionally, the plurality of chambers may be made of any suitable material.

The plurality of chambers may have a first and second outlet. The first outlet may be connected or configured to be connected to the base of the receptacle. The second outlet of the plurality of chambers may be configured to lie co-planar with the outlet of the receptacle. Such co-planarity will allow unrestricted engagement of the baffle with the outlet of the receptacle.

The plurality of chambers and the base of the receptacle may form a continuous structure. Therefore, both the plurality of chambers and the receptacle can be formed from the same mould process so that the first outlet of each chamber forms a continuous structure with the base of the receptacle.

Alternatively, the plurality of chambers may be reversibly attached to the base of the receptacle. Such engagement may occur through a snap-fit interaction between the first outlet of a chamber and the base of the receptacle.

The chambers may not be dimensioned to have a shape corresponding to the shape as the portion of soluble disinfectant composition. Accordingly, such dimensioning may include sufficient volume to allow the liquid to make contact with the total surface area of the portion of soluble disinfectant composition.

The chambers may be dimensioned to allow rotation of the one or more portion of soluble disinfectant composition, within the chamber, when immersed in a liquid. Such rotation of the one or more portions of soluble disinfectant composition within the chamber may result in improved disintegration times.

Where the chambers are not sufficiently large to allow rotation, or other movement, of the one or more portions of soluble disinfectant composition to aid disintegration, it may be beneficial to provide supports to elevate the portion of soluble disinfectant, so that the portion does not lie on the base of the receptacle and thereby restrict the in-flow and out-flow of liquid.

In an embodiment of the invention at least one of the chambers may have a side wall with inwardly extending projections to support the one or more portions of the soluble disinfect composition.

The side wall may have four inwardly extending projections, arranged in a co-planar relationship, in use. Such a configuration, will result in a suitable platform to support one or more portions of soluble disinfectant composition at an elevated position relative to the base of the receptacle.

The channels of the baffle are preferably configured to permit flow of water and aqueous disinfectant, while retaining undissolved particles of the disinfectant composition within the second compartment. Eliminating build up of disinfectant sediment onto the wipes results in wipes having safe disinfectant activity and avoids the risk of scratching surfaces being wiped.

The one or more channels may extend across the entire width or length of the baffle.

Alternatively, the one or more channels may partially extend across the width or length of the baffle. The one or more partially extending channels may form a series of connected channels.

The interior of the one or more channels may comprise a plurality of interlocking fibres.

The one or more channels may comprise one or more pores. The one or more pores may form an array which extends across the entire width or length of the baffle.

Alternatively, the one or more pores may form an array which extends partially across the width or length of the baffle. The partially extending array of pores may comprise a series of interconnected pores.

The array of pores may comprise a plurality of interlocking fibres, for example a woven or knitted fabric, needle punched felt or paper-like web.

The baffle may have a porosity in the range from 10 ppi to 60 ppi, 20 ppi to 50 ppi or 30 ppi to 40 ppi.

The one or more pores of the baffle may have diameters in the range from 0.1 μm to 10 mm, 1 mm to 5 mm, 0.1 mm to 1 mm, 0.1 μm to 20 μm or 1 μm to 5 μm.

The one or more channels of the baffle may have maximum diameters in the range from 0.1 μm to 10 mm.

Alternatively, the one or more channels of the baffle may have maximum diameters in the range from 1 mm to 5 mm, 0.1 mm to 1 mm, 0.1 μm to 20 μm or 1 μm to 5 μm.

In a preferred embodiment the baffle may have one or more microporous filter pads attached covering at least a portion of the baffle channels.

One microporous filter pad may be attached to the baffle to cover or obscure all the baffle channels.

Alternatively, one or more microporous filter pads may be arranged to overlap across the baffle, thereby covering all the baffle channels.

Alternatively, one or more microporous filter pads may be arranged to overlap across the baffle to cover only a portion of the baffle channels.

The one or more microporous filter pads may have a plurality of pores extending therethrough, the pores having diameters in the range from 0.1 μm to 50 μm.

Alternatively, the one or more microporous filter pads may have a plurality of pores extending therethrough, the pores having maximum diameters in the range from 0.1 μm to 20 μm or 0.1 μm to 10 μm In a preferred embodiment the first compartment may be sub-divided into a first and second sub-compartment, the first sub-compartment being adapted to hold wipes. The first sub-compartment being situated distally to the baffle, whilst the second sub-compartment is situated proximally to the baffle.

The outlet in the first compartment may be situated in the first sub-compartment. The outlet is positioned in the first sub-compartment to allow convenient removal of the wipes.

The first and second sub-compartments may be connected by means of a threaded engagement.

Alternatively, the first and second sub-compartments may be connected through a snap-fit engagement.

In a preferred embodiment the baffle may be adapted to be moved towards and away from the outlet of the first compartment.

The total perimeter of the baffle may remain in contact with the side wall of the container when the baffle is moved towards and away from the outlet of the first compartment. In order to maintain total perimeter contact, the user should apply pressure to the centre of the baffle. Non-central pressure applied to the baffle may result in a loss of substantial perimeter contact. Such non-central pressure is one possible mechanism to aid retrieval of the baffle from the container.

The baffle may have a width in the range from 0.1 mm to 30 mm, 0.5 mm to 25 mm or 10 to 20 mm.

The baffle may further comprise an arm. The arm may be configured to upwardly extend towards the outlet of the first compartment. The arm should have a sufficient upward length to allow a user to move the baffle towards and away from the outlet of the first compartment.

The arm may extend from the centre of the baffle. Alternatively the baffle may extend from a non-central position of the baffle.

Alternately, the arm may be further connected to the second sub-compartment of the first compartment. Such a configuration simplifies the positioning of the baffle within the container.

In a preferred embodiment the baffle is frictionally engaged with the side wall of the container.

The baffle may be frictionally engaged with the side wall of the container by means of an elastomeric material. The elastomeric material should be sufficiently deformable to mould to the side wall of the container. Such moulding should result in a fit which is resilient to the inflow and outflow of liquids and solids.

The container may contain a handle. The handle can be used to facilitate movement of the container from one surface to another. The handle may also be used as an aid to shaking the container to facilitate disintegration of the one or more portions of the soluble disinfectant composition.

The container may have a textured outer surface. The textured outer surface facilitates handling of the container, by a user, by providing a surface with additional grip.

In an embodiment of the invention the baffle is or comprises a filter. The filter may comprise open cellular material. The open cellular material may be configured to permit a flow of aqueous disinfectant, while retaining undissolved particles of the disinfectant composition within the second compartment. The open cellular material has been found to be effective in retaining fine undissolved particles. Use of cellular material allows for fast and efficient transfer of aqueous disinfectant between the compartments.

It will be appreciated that the filter of the baffle may have one or more properties and/or features of the baffle as described.

The open cellular material may comprise a natural or synthetic sponge material.

In an alternative embodiment the filter may be a bag composed wholly or partially of porous filter material. The filter bag may be configured to hold an array of wipes and may include one or more outlets. In such an embodiment the interior of the filter bag defines the first compartment.

The filter bag may be manufactured so that the array of wipes are incorporated into the filter bag during the manufacturing process.

In an alternative embodiment the filter bag may be configured to hold one or more portions of a disinfectant compositions. In such an embodiment the interior of the filter bag defines the second compartment.

The filter bag may be manufactured so that the one or more portions of disinfectant composition are incorporated into the filter bag during the manufacturing process.

The one or more wipes may be in contact with the filter. Removal of a wipe in contact with the filter facilitates entry of aqueous disinfectant into the first compartment. Without being bound to theory it is believed that this is achieved through capillary action. Accordingly, the greater the surface area of the wipe in contact with the filter the more pronounced the effect.

In an embodiment of the invention the wipes are provided in a roll having an axially extending channel, the filter being located in the channel. This results in a greater surface area of the innermost wipe being in contact with the filter.

The filter may extend along the entire length of the axially extending channel. The filter may protrude from one or both ends of the axially extending channel.

In an alternative embodiment of the invention the wipes are provided in a roll having an axially extending channel, the filter being located at the base of the receptacle.

The filter may comprise one or more rebates located in an upper surface. The rebates may be dimensioned to allow for more efficient flow of aqueous disinfectant from the second compartment into the first compartment. Alternatively, the rebates may be sufficiently dimensioned to receive one or more portions of disinfectant composition.

Alternatively the one or more rebates of the upper surface may not be dimensioned to have a shape corresponding to the shape as the portion of soluble disinfectant composition. Accordingly, such dimensioning may include sufficient volume to allow the liquid to make contact with the total surface area of the portion of soluble disinfectant composition.

The one or more rebates of the upper surface may be dimensioned to allow rotation of the one or more portions of soluble disinfectant composition, within the one or more rebates, when immersed in a liquid for example when the container is shaken. Such rotation of the soluble disinfectant composition within the one or more rebates may result in improved disintegration times.

The filter may comprise one or more rebates in its lower surface, wherein the rebates are dimensioned to house one or more portions of disinfectant composition.

The one or more rebates of the lower surface may not be dimensioned to have a shape corresponding to the shape as the portion of soluble disinfectant composition. Accordingly, such dimensioning may include sufficient volume to allow the liquid to make contact with the total surface area of the portion of soluble disinfectant composition.

The one or more rebates of the lower surface may be dimensioned to allow rotation of the one or more portion of soluble disinfectant composition, within the one or more rebates, when immersed in a liquid. Such rotation of the soluble disinfectant composition within the one or more rebates may result in improved disintegration times.

The filter may comprise a plurality of legs arranged to elevate the filter above the base of the container. Elevation of the filter allows for free movement of the soluble disinfectant composition to aid disintegration. The portion of the disinfectant is a solid dosage form comprising:
a peroxy activator; and a peroxy compound;
selected so that addition of the dosage form to a predetermined quantity of water produces a disinfectant solution containing peracetic acid in a concentration of at least about 1000 ppm when the container is filled with water to a predetermined level which covers a quantity of wipes therein.

Advantageous embodiments of this invention further comprise a colour indicator system arranged to provide a first colour signal when the concentration of peracetic acid is lower than about 1000, a second colour signal when the concentration is higher than about 1000 ppm, and a third colour signal when the concentration falls below about 1000 ppm.

The formulation of the indicator system may be arranged so that the second colour of the standing solution is maintained for at least 24 hours at an ambient temperature. In a preferred embodiment of the invention a plurality of dosage forms may be provided, each having a composition arranged to provide a working concentration of peracetic acid for a predetermined period.

A first dosage form may have a working life of 1 hour, a second may have a working life of 4 hours and a third 24 hours. In this way a user may select one or more dosage forms to give a desired working lifetime for the disinfectant composition dependent on the direction of use of the wipes.

The third colour signal may be a change from coloured, for example red, to colourless.

The peroxy activator is preferably a compound or mixture of compounds which produces an acetyl moiety when the dosage form is added to water.

A particularly advantageous peroxy activator is tetra acetyl ethylene diamine (TAED). Alternative compounds are selected from the group consisting of: 4-(acetoxy)-benzenesulfonic acid, potassium salt; 4-(acetoxy)-benzenesulfonic acid, sodium salt; 4-(octanoyloxy)-benzenesulfonic acid, sodium salt; 4-(t-butanoyloxy)-benzenesulfonic acid, sodium salt; N-[4-(triethylammoniomethyl)benzoyl]caprolactam chloride) (TBCC); sodium nonanoyloxybenzenesulfonate (NOBS) and mixtures thereof.

The amount of peroxy activator may be from about 11 wt % to 60 wt % of the solid dosage form, 20 wt % to 55 wt %, or 30 wt % to 50 wt %.

Percentages or other amounts referred to in this specification are by dry weight unless indicated otherwise and are selected from any ranges quoted to total 100%.

The peroxy compound which may be a peroxide is preferably selected from the group consisting of: sodium, potassium and ammonium salts of anions selected from the group consisting of: percarbonate, persulphate, perborate, perphosphate and mixtures thereof. Alternative peroxides include carbamide peroxide.

Particularly preferred peroxy compounds are selected from the group consisting of: sodium percarbonate, ammonium persulphate; calcium percarbonate; magnesium percarbonate; sodium perborate; sodium persulfate; sodium perphosphate; urea peroxide; and mixtures thereof.

Sodium percarbonate is particularly preferred and has favourable health and environmental properties.

Preferred dosage forms produce solutions which provide and maintain a concentration of at least 1000 ppm of peracetic acid for a period of 24 hours or longer. For example, concentrations of up to 1500 ppm or higher, for example up to 2000 ppm, can be obtained.

The ratio by weight of TAED to peroxide or peroxy compound is 50-70:100; preferably 40-80:100; 55-65:100; or 60:100.

The dosage form may be provided in the form of a tablet, for example, a compressed tablet or lozenge. An effervescent couple may be employed to facilitate dissolution. A disintegrant may be employed, for example polyvinyl pyrollidose. The amount of the disintegrant may be selected to provide a dosage form with a particular working lifetime.

Alternatively, the dosage form may be provided as a powder contained in a capsule, sachet, pouch or other container. The container may be formed from a water soluble material, for example, poly vinyl alcohol. An example of a suitable water soluble thermoplastic film is Monosol® M8900.

The disinfectant composition described above may be provided in 25 g doses, or other suitable amounts such as 5 g or 10 g, in individual sachets or pouches.

Dosage forms in accordance with this invention may provide several advantages over prior art chlorine based disinfectants. The user does not have to touch the disinfectant composition, thereby providing a health and safety benefit, in comparison to chlorine tablets which may be handled by a user.

The use of a sachet or pouch facilitates delivery of a metered dose of the ingredients. This eliminates user inconsistencies and avoids a need for measurement of powdered formulations.

The sachets and contents may dissolve within a short time in warm water, giving a disinfectant solution which gains maximum potency within a few minutes and maintains that level of potency over several hours. Tablets may take significantly longer to dissolve.

The disinfectant composition in the form of a tablet can be dissolved in 1000 ml water at 35-40° C. The disinfectant composition can destroy microbial contamination, including spores such as *Clostridium difficile* 027. There is no contact with the active ingredient by the users. When the disinfectant composition is provided as a disinfectant system in a pouch or sachet, the ingredients are not compacted and therefore dissolve quicker than other forms. This leads to quicker release of the active ingredients. Also, the provision of the disinfectant composition in sachet, pouch or tablet form provides ease of usage and ease of storage.

The solution of peracetic acid is active against most pathogens even under "dirty" conditions in which interfering grime, protein and human detritus may be present.

The colour indicator system may comprise one or more indicator compounds. A preferred indicator system comprises a mixture of:
1. 2-naphthalenesulfonic acid, 6-hydroxy-5-((2-methoxy-5methyl-4-sulfophenyl)azo)-, disodium salt (also referred to as C116035, Allura Red C); and
2. Acid Violet 43.

Colour change is used to indicate the attainment of a desired concentrates of peracetic acid and the length of time that the required concentration of 1000 ppm is maintained. Initially the solution may be purple. After 5 mins the solution may turn red indicating that working concentration of 1000 ppm has been reached. The solution changes from red to clear to indicate that the level of peracetic acid has fallen below 1000 ppm and is no longer affective against spores. Alternative indicator systems may be employed.

The composition may further comprise a chelating agent. Preferred chelating agents are selected from the group consisting of ethylenediaminetetracetic acid (EDTA), phosphones and mixtures thereof. Disodium or dipotassium EDTA may be used.

Diethylenetriamine penta(methylenephosphonic acid) sodium salt (DTPA) is an alternative preferred chelating agent. An amount of the chelating agent of 0.01 wt % to 1 wt %, preferably 0.01 wt % to 0.5 wt %, more preferably 0.09 wt % to 0.30 wt % may be used.

Alternative or additional chelating agents may be selected from the group consisting of: calcium disodium ethylene diamine tetra-acetate (E385); glucono delta-lactone (E575); sodium gluconate (E576); potassium gluconate (E577); sodium tripolyphosphate; sodium hexametaphosphate (E452i) and mixtures thereof. Alternatively, NTA, ethylenediaminetetracetic acid (EDTA), BAPTA, pentetic acid and mixtures thereof may be used.

The chelating agent may serve to reduce the presence of free transition metal ions since these may catalyse release of oxygen from active peroxide species in the solution.

The composition may further comprise an anionic surfactant. Anionic surfactants which may be used, are selected from the group consisting of a fatty alcohol sulphate, fatty alcohol phosphate, fatty alcohol benzene sulphonate, sodium and potassium salts of fatty acids, fatty alcohol ether sulphates; olefin sulphonates, lignosulphonates; sodium lauryl sulphate, phosphate esters and sarcosinates. Preferred anionic surfactants are sodium dodecyl benzene sulphonate, benzene sulfonic acid and sodium salt/sodium toluenesulphate.

Alternatively, a non-ionic surfactant may be used. These may be selected from the group consisting of ethoxylated and propoxylated fatty alcohols, ethoxylated and propoxylated alkyl phenols, fatty acid esters, polyethylene glycol esters, alkyl glucosides, glyceryl and polyglyceryl esters, ethoxylated/propoxylated copolymers, ethoxylated thiols, glucose and sucrose esters, sugar esters, sorbitan esters, ethoxylated glucose and sucrose esters, ethoxylated sugar esters, ethoxylated sorbitan esters, linear and branched fatty alcohol (N-substituted) pyrrolidone derivatives. A preferred surfactant may comprise a fatty alcohol glucoside or an N-substituted pyrrolidone, for example, a C8-N-substituted pyrrolidone (or n-octyl pyrrolidone).

The surfactant may be present in an effective concentration, for example 0.01 wt % to 1.5 wt %, preferably 0.1 wt % to 0.3 wt %, more preferably 0.15 wt % to 0.25 wt %.

The composition may also comprise a corrosion inhibitor, for example, a triazole compound. The corrosion inhibitor may be present in the disinfectant composition in an amount in the range of 0.01 wt % to 0.5 wt %, preferably in the range of 0.1 wt % to 0.3 wt %, more preferably in the range of 0.15 wt % to 0.25 wt %. The corrosion inhibitor may be present in the disinfectant composition in an amount of 0.2 wt %. A suitable corrosion inhibitor is sold by Brad-Tech Ltd. under the trade mark BRADTECH 6030.

A pH modifier or buffer may be employed. The pH modifier may comprise an anhydrous organic acid. This may be powdered or granular. The pH modifier may be one or more of citric acid, fumaric acid, tartaric acid, adipic acid. Anhydrous citric acid is preferred.

A disintegrate may be employed, for example, sodium carboxymethyl cellulose marketed as Nilyn XL-090.

The invention will be further described by means of example, but not in any limitative sense.

Example 1

A disinfectant composition was formed by mixing the following powdered components: —

| | wt % |
|---|---|
| TAED | 30.75% |
| sodium percarbonate | 49.0% |
| citric acid (anhydrous) | 11.04% |
| sequestrant | 0.17% |
| sodium bicarbonate | 6.9% |
| surfactant | 1.00% |
| C.I.16035 (food red 17) | 0.06% |
| C.I. 60730 (acid violet 43) | 0.1% |
| perfume | 0.01% |
| manganese sulphate | 0.025% |
| corrosion inhibitor | 0.2% |
| non-active ingredients | |
| Total | 100 |

Example 2 (1)

The following ingredients were added successively with mixing after each addition: —

| TAED | wt % |
|---|---|
| sodium percarbonate monohydrate | 41.33 |
| anhydrous citric acid | 15 |
| dipotassium ethylenediamine acetate (EDTA) | 0.34 |
| sodium lauryl sulphate | 2 |
| sodium dodecylbenzene | 0.83 |
| corrosion inhibitor (BRADTECH 6030) | 0.2 |
| Food Red 17 dye | 0.07 |
| Acid Violet dye | 0.078 |
| sodium bicarbonate | 22.22 |
| perfume | 0.2 |
| Total | 100% |

The following steps were employed:
1) Add the measure of TAED, then mix
2) Add sodium percarbonate, then mix
3) Add sodium bicarbonate, then mix
4) Add surfactants, then mix
5) Add inhibitor, then mix
6) Add sequestrant, then mix
7) Measure out the citric acid in a separate mix and then add the liquid perfume as required, keeping it apart from the main mix until dry.
8) Add the citric acid and perfume mix to the main mix, then mix
9) Add the first indicator dye, then mix.
10) Add the second indicator dye, then mix.
11) Mixing was continued to ensure that there were no lumps and an even distribution of all the ingredients was obtained.

The resultant mixtures were compressed into individual tablets. A concentration of approximately 1000 ppm of peracetic acid is sufficient to provide sporicidal action. This was achieved by dissolution of an 8 g tablet in 1 liter of water at an ambient temperature to form a solution of peracetic acid.

The sanitiser/disinfectant is an alkaline solution utilising the range of 30 wt % TAED to 50 wt % percarbonate.

After thoroughly blending the mixture described in the Examples was pressed into tablets having a size that can be used in combination or singularly to produce 1000 ppm peracetic acid in 1 liter of water. For example, an 8 g tablet is used to produce the desired concentration in 1 liter of water.

Wipes impregnated with the product was suitable for disinfecting and sanitising surfaces in hospital wards, environmental, clinical and laboratory surfaces, as well as heat sensitive equipment such as dialysis instruments, surgical instruments, suction bottles, bronchoscope, autoclaves and ear, nose, and throat instruments. Wipes impregnated with the product can also be used to disinfect surfaces that have been contaminated by body fluids.

FIG. 1 shows a container (1) engaged with a baffle (2). The container (1) comprises a base (3) and side wall (4). When the baffle (2) is inserted into the container (1) the container (1) is thereby divided into a first (5) and second (6) compartment. The first compartment (5) is further subdivided into a first (7) and second (8) sub-compartment. The first sub-compartment (7) comprises an upper surface (9) with an outlet (10), side wall (11) and a lower surface (12). The one or more portions of soluble disinfectant (13) are rested to on the interior surface (14) of the container's base (3). The lower surface (12) of the first sub-compartment (7) is configured to engage with an upper surface (15) of the second sub-compartment (8). The lower surface (12) of the first sub-compartment (7) is further configured to allow the inflow and outflow of liquid. The first sub-compartment (7) is sufficiently dimensioned to hold an array of wipes. The wipes are removed from the first sub-compartment (7) through the outlet (10) of the first sub-compartment (7). The lower surface (12) of the first sub-compartment (7) is connected to an arm (16) at the first end (17) of the arm (16), whilst the second end (18) of the arm (16) is connected to the baffle (2). The baffle (2) comprises an upper surface (19) and lower surface (20) with a plurality of channels (21) running there through. The channels (21) allow the in-flow and out-flow of liquid whilst restricting the passage of solid particulate. The perimeter (22) of the baffle (2) comprises an elastomeric material (22a) which is dimensioned to contact the interior surface (23) of the container's side wall (4) through its total surface area. Said contact results in a frictional engagement between the perimeter (22) of the baffle (2) and the interior surface (23) of the container's side wall (4), thereby resulting in a liquid and solid resilient barrier.

Figure 2:
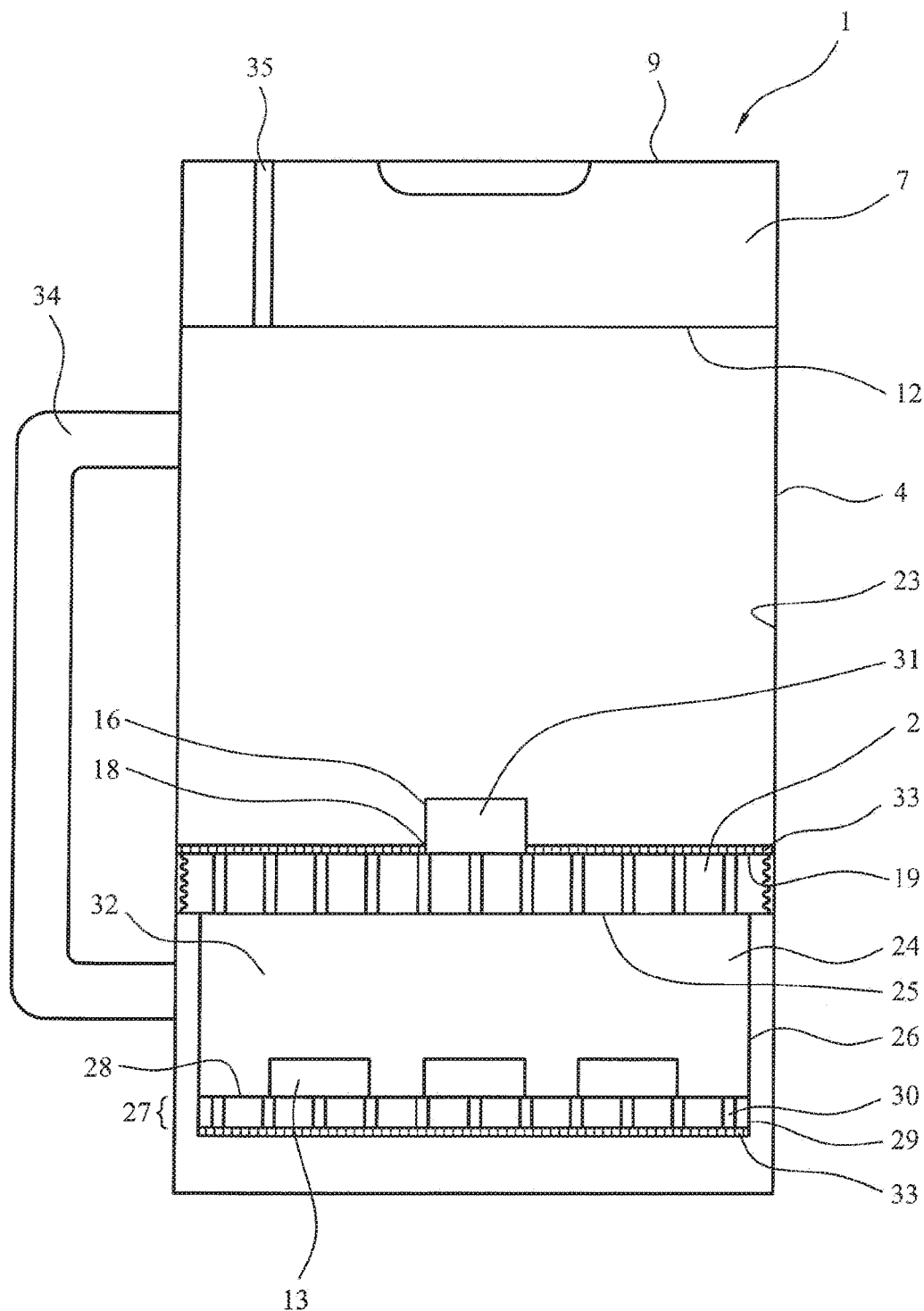
FIG. 2 shows a side view of the container where the baffle is engaged with a receptacle, wherein the receptacle is suitably dimensioned to hold one or more portions of soluble disinfectant.

With reference to FIG. 1, FIG. 2 shows a baffle (2) connected to a receptacle (24) whilst being frictionally engaged with the interior surface (23) of the container's side wall (4). The receptacle (24) comprises an outlet (25), side wall (26) and base (27). The receptacle's base (27) has an interior (28) and exterior (29) surface with channels (30) running there through. The channels (30) of the receptacle (24) allow the in-flow and out-flow of liquid, whilst restricting the outflow of solid particulate. The upper surface (19) of the baffle (2) is connected to an arm (16) at the arm's second end (18), whilst the first end (31) of the arm (16) is configured to be manipulated by a user's fingers and thereby move the baffle (2) up and down the container (1). The interior (32) of the receptacle (24) is sufficiently dimensioned to allow one or more portions of disinfectant composition (13) to lie on the interior surface (28) of the receptacle's base (27). Micro porous filter pads (33) are attached to the upper surface (19) of the baffle (2) and the exterior surface (29) of the receptacle's base (27). Attachment of the micro porous filter pads (33) results in the channel's (30) exits being covered. The micro porous filter pads (33) allow the inflow and outflow of liquid, whilst restricting the outflow of solid particulate. Furthermore, as the micro porous filter pads (33) allow a more efficient barrier to solid particulate, addition of the micro porous filter pads (33) to the receptacle (24) and baffle (2) will provide a more efficient filtering system. The container (1) comprises a handle (34) attached to the side wall (4) of the container (1) to allow the user to handle the container (1) with ease. The container (1) further comprises an outlet (35) which extend between the lower (12) and upper (9) surface of the first sub-compartment (7). The outlet (35) prevents the build-up of gas, by allowing the gas to pass through the outlet (35) and into the external environment.

Figure 3:
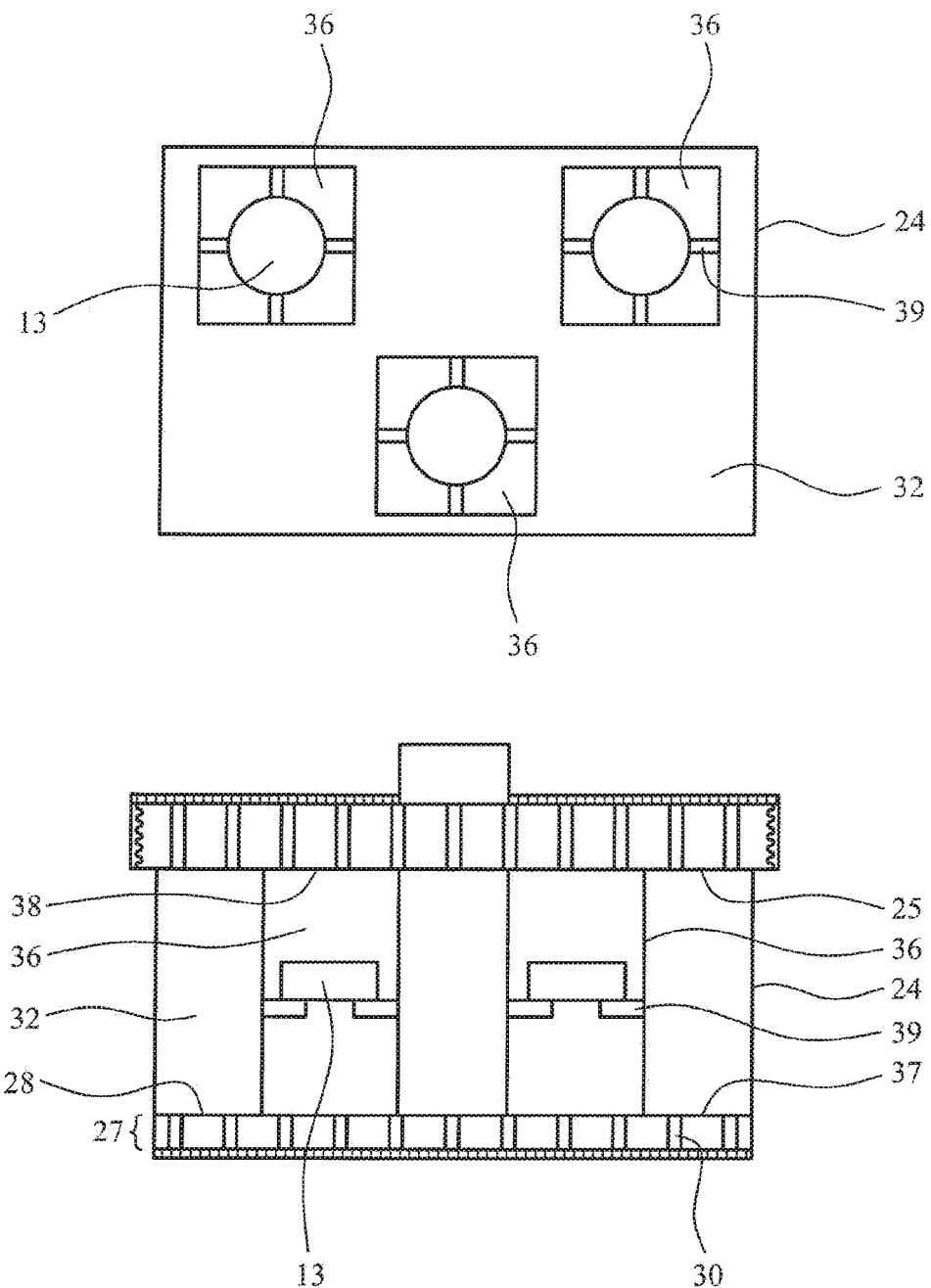
FIG. 3 shows a side and plan view of the receptacle.

With reference to FIG. 1 and FIG. 2, FIG. 3 shows an alternative version of the receptacle (24). The receptacle (24) comprises three chambers (36) located within the interior (32) of the receptacle (24). Each chamber (36) comprises a first (37) and second outlet (38). The first outlet (37) being configured to be connected to the interior surface (28) of the receptacles base (27), whilst the second outlet (38) is configured to lie co-planar with the outlet (25) of the receptacle (24). Each chamber (36) further comprises four inwardly extending projections (39), which extend from the side wall (40) of the chambers (36). The inwardly extending projections (39) being in a co-planar relationship and orientated towards a central axis resulting in an angle of 90° to each of the inwardly extending projection's neighbours. Such a configuration allows the one portion of soluble disinfectant composition (13) to lie upon the inwardly extending projections (39). The inwardly extending projections (39) are located at the mid-point in the chamber (36). Such positioning allows the one portion of soluble disinfectant composition (13) to be held above the interior surface (28) of the receptacle's base (27) and thereby avoiding the restriction of the passage of liquid through the receptacle channels (30).

Figure 4:
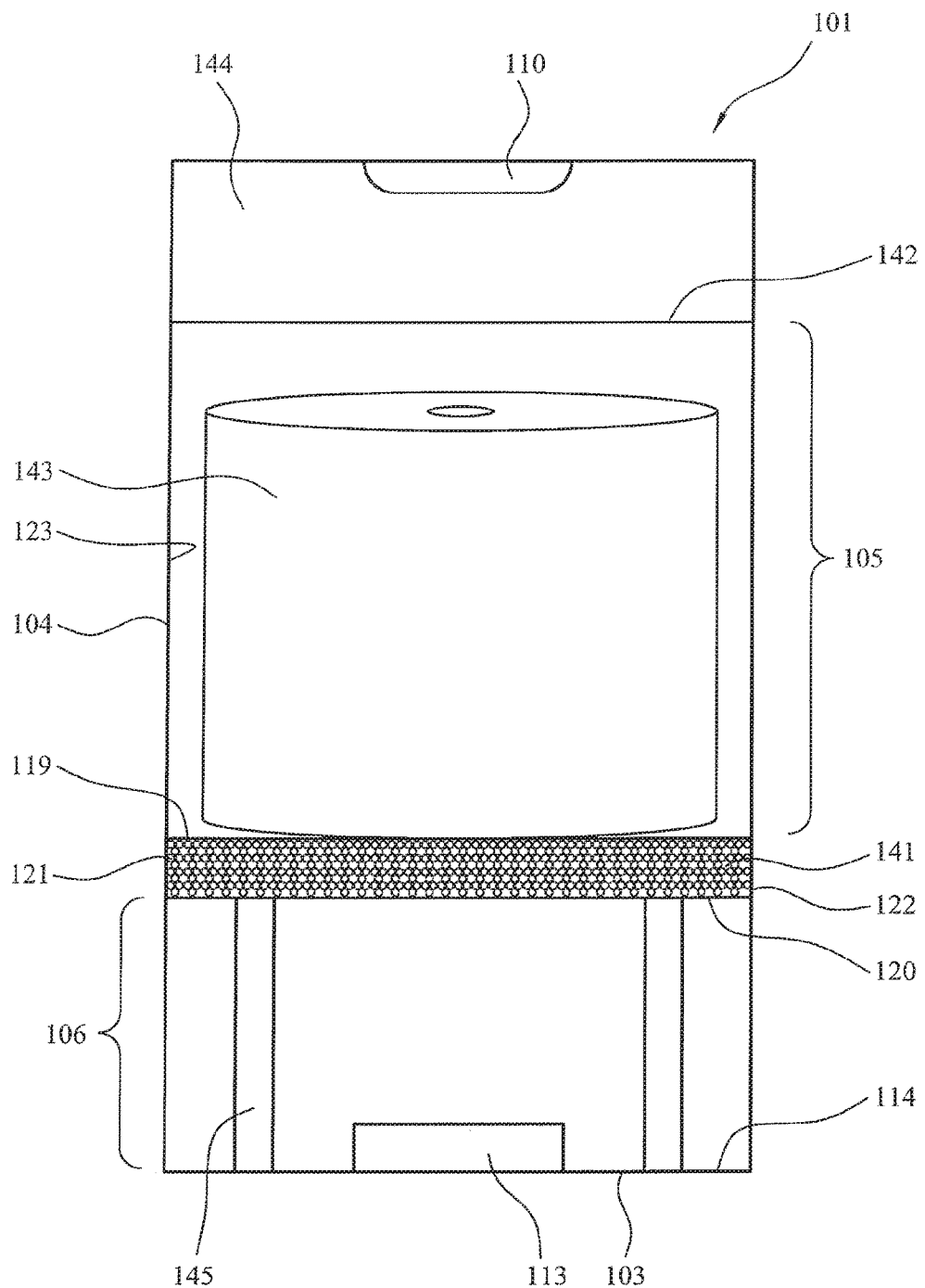
FIG. 4 shows a side view of the container with an elevated filter at the base of the container.

FIG. 4 shows a container (101) engaged with a filter (141). The container comprises a base (103), a side wall (104) and an upper rim (142). When the filter (141) is inserted into the container (101) the container (101) is thereby divided into a first (105) and second compartment (106). The first compartment (105) is sufficiently dimensioned to hold an array of wipes (143). A portion of soluble disinfectant (113) is rested on the interior surface (114) of the second compartments base (103). The container (101) further comprises a lid (144). The lid (144) is configured to connect to the upper rim (142) of the first compartment (105). The wipes are removed from the first compartment (105) through an outlet (110) of the lid (144). The filter (141) comprises an upper surface (119) and lower surface (120) with a plurality of channels (121) running therethrough. The channels (121) allow the in-flow and out-flow of liquid whilst restricting the passage of solid particulates from the second compartment (106) to the first compartment (105). The perimeter (122) of the filter (141) is configured to frictionally engage the interior surface (123) of the container side wall (104), thereby resulting in a liquid and solid resilient barrier. The filter (141) further comprises a plurality of legs (145) which are attached to the lower surface (120) of the filter (141). The legs (145) are configured to engage the base (103) of the second compartment (106). Elevation of the filter (141) allows for movement of the soluble disinfectant composition (113) to aid disintegration.

Figure 5:
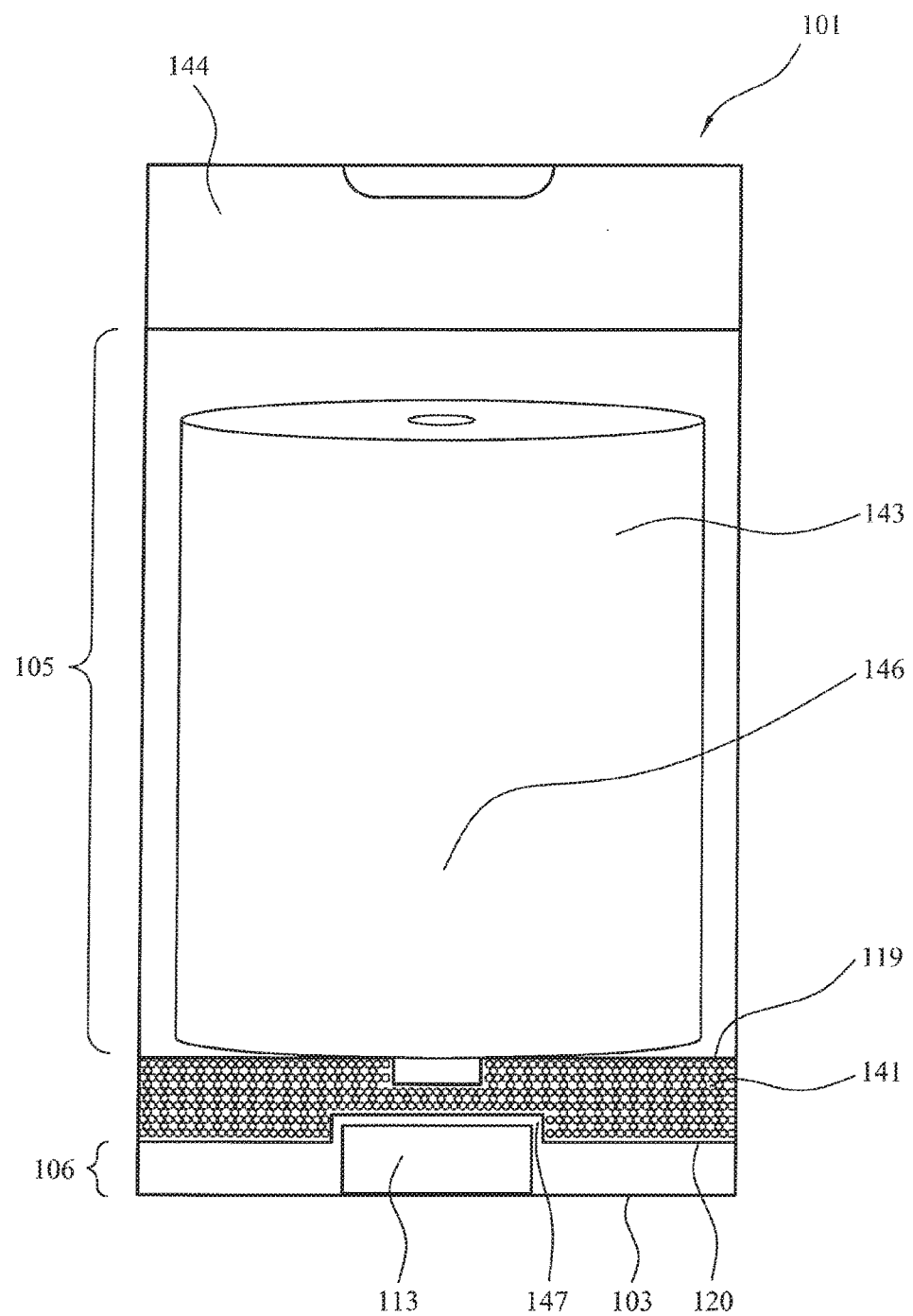
FIG. 5 shows a side view of the container with a filter at the base of the container, the filter comprising rebates.

FIG. 5 shows the container of FIG. 4 with an alternative filter (141). The filter (141) comprises a rebate (146) in its upper surface (119) and a rebate (147) in its lower surface (120). The rebate (147) in the lower surface (120) is dimensioned to house a portion of solid disinfectant composition (113). The rebate (147) allows for movement of the solid disinfectant composition (113) to aid disintegration upon addition of water. The rebate (146) in the upper surface (119) allows for efficient flow of aqueous disinfectant from the second compartment (106) into the first compartment (105).

In use, the lid (144) is detached from the first compartment (105). The filter (141) is then removed. One or more portions of solid disinfectant (113) are placed on the base (103) of the container (101). The filter (141) is then placed at the base (103) of the container (101). A roll of wipes (143) is then positioned on top of the filter (141). Water is then added to the container (101) in a sufficient amount to at least cover the filter (141). Finally, the lid (144) is reattached to the first compartment (105). Sediment free wipes containing aqueous disinfectant are then removed from the container through the outlet (110) of the lid (144).

Figure 6:
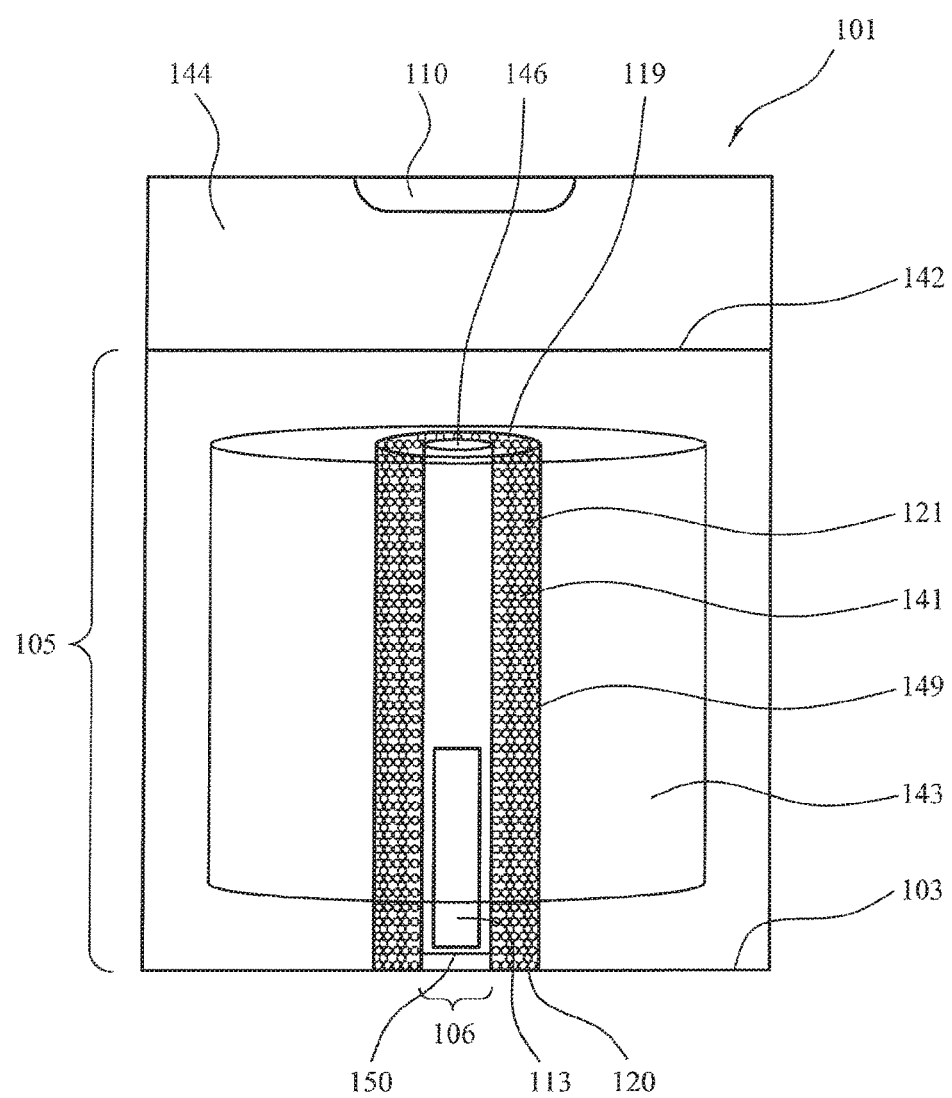
FIG. 6 shows a part cross-sectional view of the container with a filter, the filter being located within an axially extending channel of the roll of wipes.

FIG. 6 shows a container (101) engaged with a filter (141). The container comprises a base (103), a side wall (104) and an upper rim (142). When the filter (141) is inserted into the container (101) the container (101) is thereby divided into a first (105) and second compartment (106). The first compartment (105) is sufficiently dimensioned to hold an array of wipes (143). The filter (141) is an elongated tube with an upper surface (119), a lower surface (120) and circumferentially extending walls (149). The lower surface (120) is configured to rest on the base (103) of the container (101). A rebate (146) is located in the upper surface (119) of the filter (141). The rebate (146) extends downwardly through the filter (141). The base (150) of the rebate (146) is proximate to the lower surface (120) of the filter (141). The rebate (146) partially defines the second compartment (106). A portion of soluble disinfectant (113) is rested within the second compartment (106). The container (101) further comprises a lid (144). The lid (144) is configured to connect with the upper rim (142) of the first compartment (105). The wipes (143) are removed from the first compartment (105) through an outlet (110) of the lid (144). The circumferentially extending walls (149) of the filter (141) comprise a plurality of channels (121) running there through. The channels (121) allow the in-flow and out-flow of liquid whilst restricting the passage of solid particulate from the second compartment (106) to the first compartment (105).

In use, the lid (144) is detached from the first compartment (105). The filter (141) is then removed. One or more portions of solid disinfectant (113) are placed in the rebate (146) of the filter (141). The filter (141) is then inserted into the centre of a roll of wipes (143). The roll of wipes (143) is then placed onto the base (103) of the container (101). Water is then added to the container (101) in a sufficient amount to at least cover the filter (141). Finally, the lid (144) is reattached to the first compartment (105). Sediment free wipes containing aqueous disinfectant are then removed from the container through the outlet (110) of the lid (144).

Figure 7:
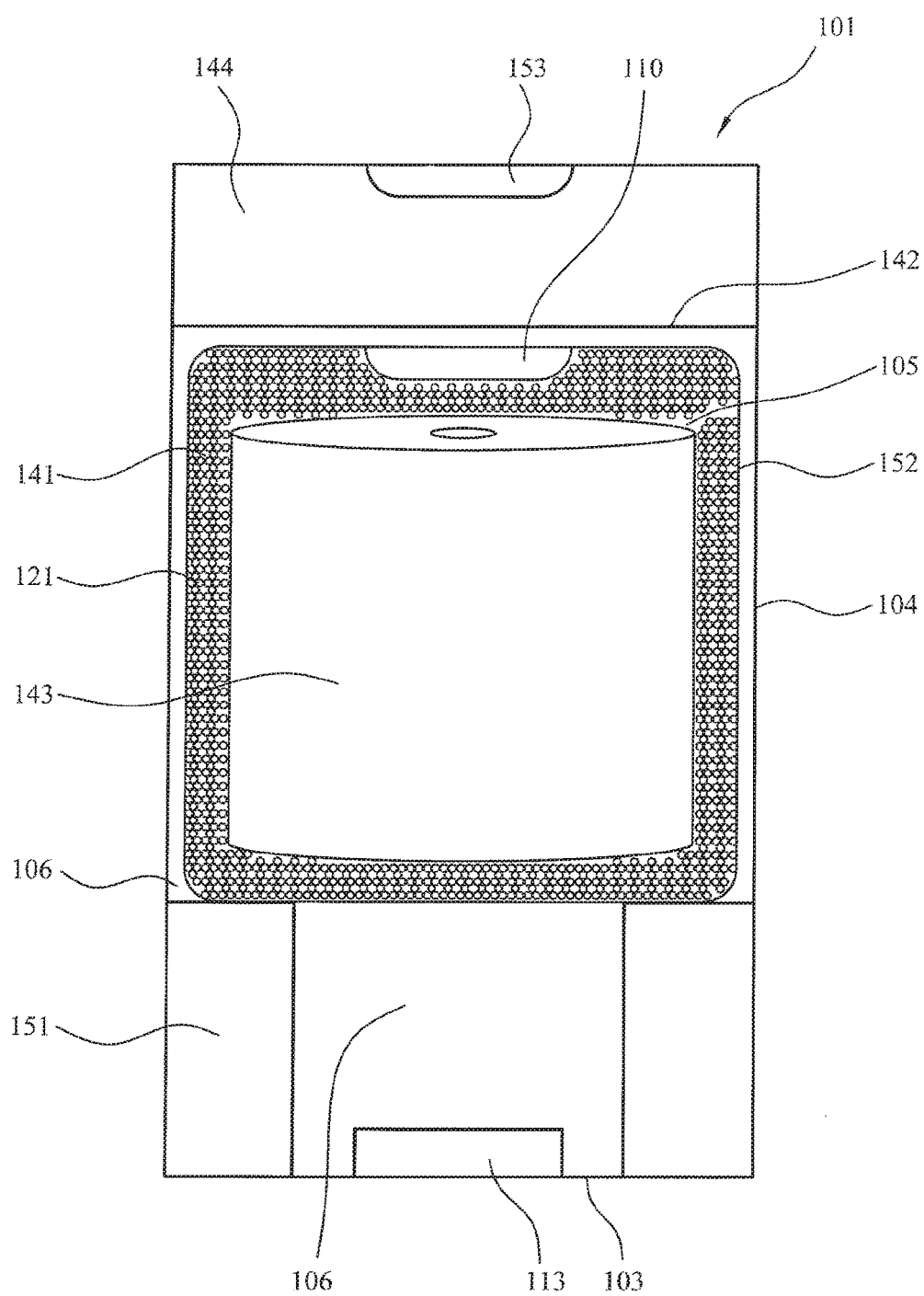
FIG. 7 shows a part cross-sectional view of a container with a filter bag.

FIG. 7 shows a container (101) engaged with a filter (141). The container comprises a base (103), a side wall (104), an upper rim (142) and inwardly extending ridges (151). When the filter (141) is inserted into the container (101) the container (101) is thereby divided into a first (105) and second compartment (106). The filter (141) is of an enclosed bag configuration and comprises a hollow core/first compartment (105) and an outer wall (152). The hollow core/first compartment (105) is sufficiently dimensioned to hold an array of wipes (143). The outer wall (152) of the filter (141) comprises a single outlet (110). The filter (141) is configured to rest on the inwardly extending ridges (151) of the container (101) so that the single outlet (110) is proximate to an opening (153) in the container's lid (144). The lid (144) is configured to connect with the upper rim (142) of the second compartment (106). A portion of soluble disinfectant (113) is rested at the base (103) of the container (101). The wipes (143) are removed through an outlet (110)

of the first compartment (105) and through an opening (153) of the lid (144). The outer wall (152) of the filter (141) includes a plurality of channels (121) extending therethrough. The channels (121) allow the in-flow and out-flow of liquid whilst restricting the passage of solid particulate from the second compartment (106) to the first compartment (105).

In use, the lid (144) is detached from the second compartment (106). One or more portions of solid disinfectant (113) are placed on the base (103) of the container (101). The filter (141), containing wipes (143), is then placed on the inwardly extending ridges (151) of the container (101). Water is then added to the container (101) in a sufficient amount to at least partially cover the filter (141). Finally, the lid (144) is reattached to the second compartment (106). Sediment free wipes containing aqueous disinfectant are then removed through the outlet (110) of the first compartment (105) and through the opening (153) of the lid (144).

Figure 8:
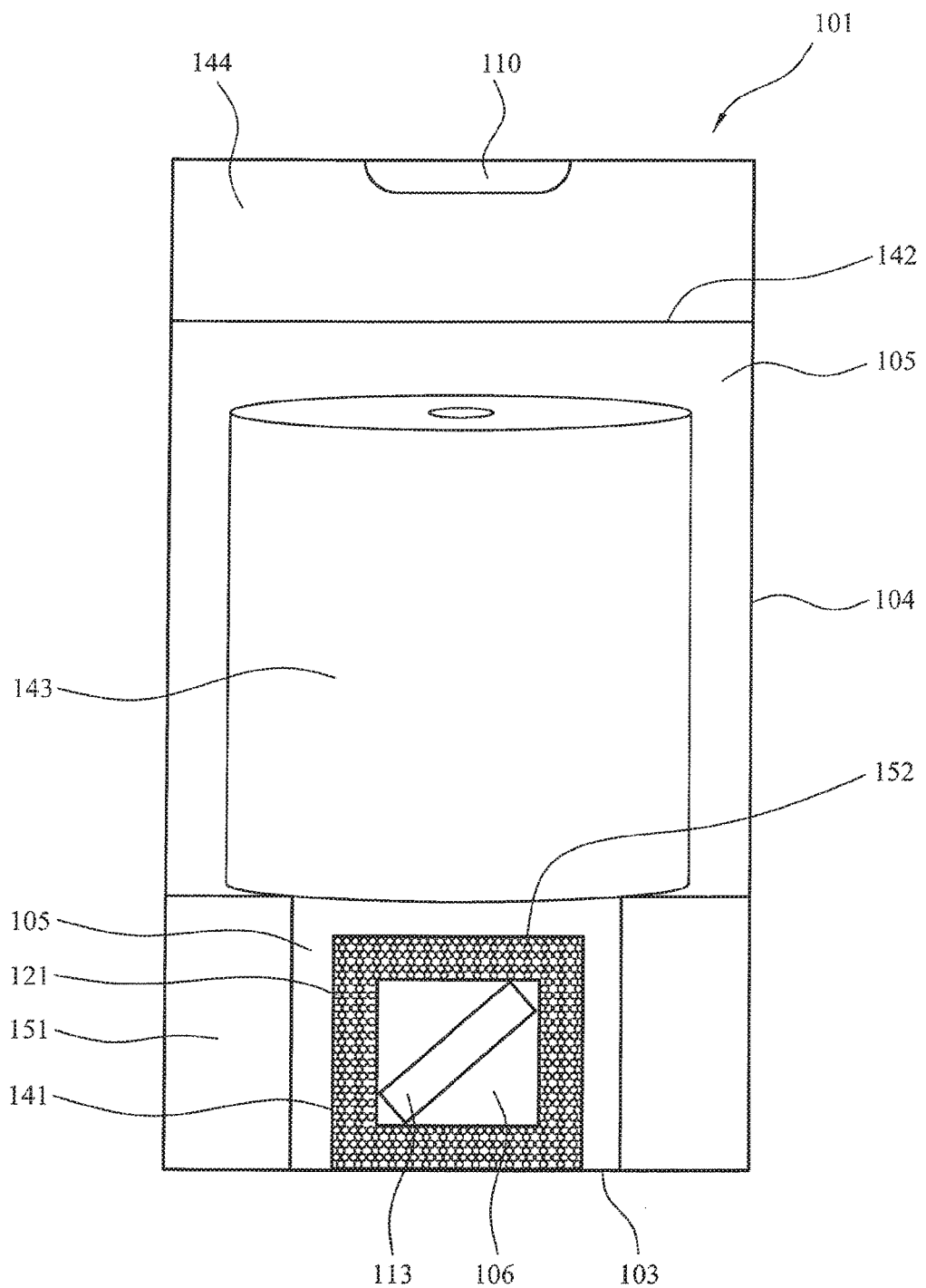
FIG. 8 shows a part cross-sectional view of a container with an alternative filter bag.

FIG. 8 shows a container (101) engaged with a filter (141). The container comprises a base (103), a side wall (104), an upper rim (142) and inwardly extending ridges (151). When the filter (141) is inserted into the container (101) the container (101) is thereby divided into a first (105) and second compartment (106). The filter (141) is of an enclosed bag configuration and comprises a hollow core/second compartment (106) and an outer wall (152). The hollow core/second compartment (106) is sufficiently dimensioned to hold one or more portions of solid disinfectant composition (113). The filter (141) is shown at rest on the base (103) of the container (101). The wipes (143) are configured to rest on the inwardly extending ridges (151) of the container (101). The lid (144) is configured to connect with the upper rim (142) of the second compartment (106). The wipes (143) are removed through an outlet (110) of the lid (144). The outer wall (152) of the filter (141) includes a plurality of channels (121) extending therethrough. The channels (121) allow the in-flow and out-flow of liquid whilst restricting the passage of solid particulate from the second compartment (106) to the first compartment (105).

In use, the lid (144) is detached from the first compartment (105). The filter bag (141) with enclosed disinfectant portions (113) is placed on the base (103) of the container (101). The wipes (143) are then placed on the inwardly extending ridges (151) of the container (101). Water is then added to the container (101) in a sufficient amount to at least partially cover the filter (141). Finally, the lid (144) is reattached to the first compartment (105). Sediment free wipes containing aqueous disinfectant are then removed through the outlet (110) of the first compartment (105).

I claim:

1. A disinfectant wipe dispenser comprising:
a container having first and second compartments, the first compartment being dimensioned to store a supply of wipes in use;
the first and second compartments being separated by a baffle, the baffle including one or more channels communicating between the compartments;
the first compartment having an outlet through which wipes may be successively drawn; and,
the second compartment being dimensioned to receive one or more portions of a disinfectant composition, the disinfectant composition comprising a peroxy activator, a peroxy compound and optional further excipients, selected so that addition of the dosage form to a predetermined quantity of water produces a disinfectant solution containing peracetic acid at a concentration of at least about 1000 ppm;
wherein
wherein the baffle is a filter;
the channels communicate between the compartments and allow flow of water and aqueous disinfectant between the compartments; and,
the channels have a maximum dimension configured to prevent movement of particles of disinfectant sediment from the second compartment to the first compartment.

2. A disinfectant wipe dispenser as claimed in claim 1, further including a receptacle, the receptacle comprising: a side wall, outlet, base and one or more channels through which aqueous disinfectant may flow; the outlet of the receptacle being configured to engage with the baffle.

3. A disinfectant wipe dispenser as claimed in claim 2, wherein the one or more channels extend through the base of the receptacle.

4. A disinfectant wipe dispenser as claimed in claim 2, wherein the one or more channels extend through the side wall of the receptacle.

5. A disinfectant wipe dispenser as claimed in claim 2, wherein the receptacle includes one or more microporous filter pads covering at least a portion of the channels.

6. A disinfectant wipe dispenser as claimed in claim 2, wherein the receptacle contains a plurality of chambers, each being dimensioned to receive at least the one portion of soluble disinfectant composition.

7. A disinfectant wipe dispenser as claimed in claim 6, wherein the chamber has a side wall with inwardly extending projections to support the one or more portions of the soluble disinfectant composition.

8. A disinfectant wipe dispenser as claimed in claim 1, further comprising one or more microporous filter pads covering at least a portion of the baffle channels.

9. A disinfectant wipe dispenser as claimed in claim 1, wherein the first compartment is sub-divided into a first and a second sub-compartment, the first sub-compartment being adapted to hold wipes.

10. A disinfectant wipe dispenser as claimed in claim 1, wherein the baffle is adapted to be moved towards and away from the outlet of the first compartment.

11. A disinfectant wipe dispenser as claimed in claim 1, wherein the filter comprises open cellular material.

12. A disinfectant wipe dispenser as claimed in claim 11, wherein the open cellular material comprises a sponge.

13. A disinfectant wipe dispenser as claimed in claim 1, wherein one or more wipes is in contact with the filter.

14. A disinfectant wipe dispenser as claimed in claim 1, wherein the wipes are provided in a roll having an axially extending channel, the filter being located in the channel.

15. A disinfectant wipe dispenser as claimed in claim 1, wherein the wipes are provided in a roll having an axially extending channel, the filter being located at the base of the receptacle.

16. A disinfectant wipe dispenser as claimed in claim 1, further comprising a colour indicator arranged to provide a first colour signal when the concentration of peracetic acid is lower than about 1000 ppm and a second colour signal when the concentration is higher than about 1000 ppm and a third colour signal when the concentration falls below about 1000 ppm.

17. A disinfectant wipe dispenser as claimed in claim 1, wherein the peroxy activator is selected from the group consisting of: tetraacetylethylenediamine, 4-(acetoxy)-benzenesulfonic acid, potassium salt; 4-(acetoxy)-benzenesulfonic acid, sodium salt; 4-(octanoyloxy)-benzenesulfonic acid, sodium salt; 4-(t-butanoyloxy)-benzenesulfonic acid, sodium salt; N-[4-(triethylammoniomethyl)benzoyl] caprolactam chloride) (TBCC); sodium nonanoyloxybenzenesulfonate (NOBS) and mixtures thereof.

18. A disinfectant wipe dispenser as claimed in claim 17, wherein the peroxy activator is tetra acetyl ethylenediamine (TAED).

19. A disinfectant wipe dispenser as claimed in claim 1, wherein the peroxy compound is sodium percarbonate.

* * * * *